(12) United States Patent
Raman et al.

(10) Patent No.: US 10,245,378 B2
(45) Date of Patent: Apr. 2, 2019

(54) RESERVOIR VOLUME SENSING

(71) Applicant: Medtronic, Inc., Minneapolis, MN (US)

(72) Inventors: Naresh Lakshman Raman, Shanghai (CN); Alex O. Espe, Minneapolis, MN (US); Nicholas R. Whitehead, Lake Elmo, MN (US); Timothy J. Denison, Minneapolis, MN (US); Venkat R. Gaddam, Plymouth, MN (US); Scott A. Sarkinen, Greenfield, MN (US); Erik J. Peterson, Fridley, MN (US); Jacob A. Otterstetter, Coon Rapids, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 108 days.

(21) Appl. No.: 15/418,281

(22) Filed: Jan. 27, 2017

(65) Prior Publication Data
US 2018/0214635 A1    Aug. 2, 2018

(51) Int. Cl.
| | |
|---|---|
| G01F 17/00 | (2006.01) |
| A61M 5/172 | (2006.01) |
| A61M 5/155 | (2006.01) |
| A61M 5/152 | (2006.01) |
| A61M 5/168 | (2006.01) |
| A61M 5/142 | (2006.01) |

(52) U.S. Cl.
CPC ........ *A61M 5/172* (2013.01); *A61M 5/14224* (2013.01); *A61M 5/14276* (2013.01); *A61M 5/152* (2013.01); *A61M 5/155* (2013.01); *A61M 5/1684* (2013.01); *G01F 17/00* (2013.01); *A61M 2205/18* (2013.01); *A61M 2205/3306* (2013.01); *A61M 2205/3375* (2013.01); *A61M 2205/3389* (2013.01); *A61M 2205/3523* (2013.01); *A61M 2205/50* (2013.01); *A61M 2205/702* (2013.01); *A61M 2209/045* (2013.01)

(58) Field of Classification Search
None
See application file for complete search history.

(56) References Cited

U.S. PATENT DOCUMENTS

| | | | |
|---|---|---|---|
| 4,845,487 A | 7/1989 | Frantz et al. | |
| 6,210,368 B1 | 4/2001 | Rogers | |
| 8,083,730 B2 | 12/2011 | Miesel | |
| 8,165,676 B2 | 4/2012 | Donofrio | |
| 8,170,636 B2 | 5/2012 | Cinbis | |
| 8,561,460 B2 | 10/2013 | Miesel | |

(Continued)

OTHER PUBLICATIONS

Avago Technologies, "HSDL—9100 Surface-Mount Proximity Sensor Data Sheet", 1 pg.

(Continued)

*Primary Examiner* — Paul M. West
*Assistant Examiner* — Mark A Shabman
(74) *Attorney, Agent, or Firm* — Mueting, Raasch & Gebhardt, P.A.

(57) ABSTRACT

Reservoir volume of implantable infusion devices may be determined using a volume sensor that provides a signal representative of a distance between the volume sensor and a movable wall of the reservoir. The volume sensor may be a light-based or sound-based sensor, and may be located outside of the reservoir.

19 Claims, 6 Drawing Sheets

(56) References Cited

U.S. PATENT DOCUMENTS

| | | | |
|---|---|---|---|
| 2005/0267500 A1* | 12/2005 | Hassler, Jr. | A61F 5/0003 606/157 |
| 2012/0203177 A1 | 8/2012 | Lanier, Jr. et al. | |
| 2012/0265141 A1 | 10/2012 | Kalpin et al. | |
| 2013/0086982 A1* | 4/2013 | Miesel | A61M 5/1684 73/149 |
| 2014/0054883 A1* | 2/2014 | Lanigan | A61M 39/1011 285/33 |
| 2014/0194812 A1 | 7/2014 | Amirouche et al. | |

OTHER PUBLICATIONS

Motion Controls, LLC., www.motioncontrolsllc.com, "LED Light Based Position/Volume Sensor features of qvla", 2 pgs.
International Search Report and Written Opinion, PCT/US2018/012753, dated May 2, 2018, 13 pages.

* cited by examiner

RESERVOIR VOLUME SENSING

This disclosure generally relates to, among other things, implantable medical infusion devices, and more particularly to implantable infusion devices including a reservoir and volume sensing apparatus to measure the volume of fluids within the reservoir.

A variety of therapies exist for treating patients using implantable infusion systems. The implantable infusion systems can be used to deliver therapeutic fluids, or drugs, to a target location of a patient, such as the spinal canal, the brain, or the heart. The implantable infusion systems include implantable infusion devices that are often subcutaneously implanted in a convenient location in the patient and implantable catheters that are used to carry the therapeutic fluids from the infusion device to the target location.

Implantable infusion devices can have refillable reservoirs for housing therapeutic fluids, which can be infused over time. The reservoirs can be periodically refilled so that the implanted infusion systems can be employed for long-term use. Typically, the infusion devices have a fill port in communication with the reservoir. A refill apparatus needle can be percutaneously inserted into the fill port so that fresh therapeutic fluid can flow through the refill needle into the fill port to refill the reservoir and replenish the supply of therapeutic fluid.

Since implantable infusion devices are implanted within patients, ascertaining the volume, or fullness, of the therapeutic fluid contained with the reservoirs may be challenging, and may often utilize labor- and time-intensive methods. For example, during refill, the residual supply of therapeutic fluid, or drug, in a reservoir may be determined by evacuating, or aspirating, to the extent possible, the residual supply of therapeutic fluid, or drug, in the reservoir using a syringe, and determining the volume of the remaining therapeutic fluid from the graduations on the syringe. Such procedure may be described as being invasive and potentially painful for the patient.

SUMMARY

Throughout the life and use of an implantable infusion device, it may be advantageous to determine the volume of therapeutic fluid, or drug, contained in the reservoir. For example, clinicians who refill the reservoirs of implantable infusion devices would benefit from knowing the volume of the reservoirs prior to and during the refill procedure. Further, knowledge of the volume of the therapeutic fluid contain within the reservoirs may also increase conformance by ensuring that the reservoirs repeatedly reach a completely full status each time the reservoir is refilled. Likewise, periodic volume readings during operation may permit a physician or a patient to determine when refilling should be scheduled. Such volume data can also be used to determine or possibly predict pump or infusion system malfunctions or leaks. Further, it may be helpful for implantable infusion devices to "know" the amount of a therapeutic fluid, or drug, remaining in the reservoirs in order to provide an indication of when a refill is necessary.

It may be advantageous to provide an implantable infusion device that includes quick, easy, non-invasive, and accurate sensing of the volume of therapeutic fluid, or drug, contained in the reservoir of the device. Further, it may be beneficial to a user to be able to request a volume measurement at any time and/or at periodic times. The exemplary systems, devices, and methods disclosed herein may be described as providing a quick, easy, non-invasive, accurate, and on-demand process to measure the remaining volume of therapeutic fluid, or a drug, within a reservoir of an implanted device. Additionally, the exemplary systems, devices, and methods may be described as being able to determine the remaining volume of therapeutic fluid, or a drug, within a reservoir without relying on a number of therapy-emitting "pulses" or "pump strokes" of a known per-pulse/stroke volumetric output. Still further, the exemplary systems, devices, and methods may be described as offering a low-power method of accurately discerning the reservoir fill level for implantable infusion devices or pumps without the need for complex algorithms that may be prone to variation.

The exemplary systems, devices, and methods may include a volume sensor, which may also function as an average flow sensor, to detect and reduce consequences of over-infusion and under-infusion by, e.g., providing a non-invasive volume check to facilitate a quick and easy "system check," self-monitoring to detect over or under-dosage (e.g., in response suspected under or over-dosage), and providing the ability, or functionality, for clinicians during a refill process to observe that the therapeutic fluid, or drug, leaving a syringe is entering the reservoir. The exemplary volume sensor and methods used therewith may be described as having a resolution that is sensitive to about 0.45 milliliter (ml) change in therapeutic fluid volume in the reservoir. Further, the exemplary volume sensor and accompanying structures and apparatus may require minimal mechanical changes in existing implantable infusion devices (e.g., no changes may be made to basic reservoir design or pumping mechanisms). Additional, integration of the exemplary volume sensor and accompanying structures and apparatus to implantable infusion devices may be cost-effective and may have minimal negative impact on pump reliability while potentially improving therapy level reliability. Still further, the exemplary volume sensor may improve therapy safety by providing refill feedback, providing over/under infusion alarms/logs, and providing quicker and less invasive reservoir volume checks when troubleshooting targeted drug delivery (TDD) therapies.

It may be further described that the value of the exemplary volume sensor technology may be used as a tool to use for helping "rule out" system malfunction and/or human error when an infusion therapy patient presents with symptoms consistent with infusion accuracy error. Further, the exemplary volume-sensing technology could be valuable when integrated into a clinical refill and troubleshooting workflow. Still further, the exemplary volume-sensing technology may also improve on current methods through increased accuracy and replacement of invasive diagnostic procedures such as pump drug aspiration with simple non-invasive pump interrogation by telemetry. One or more embodiments may also provide users with alarm options such as, e.g., alarms indicating over-infusion, alarms indicating under-infusion, alarms indicating that the therapeutic fluid is low in the reservoir, and alarms indicating that the reservoir is empty.

One exemplary implantable medical infusion device may include a housing and an expandable reservoir located in the housing to contain therapeutic fluid. The expandable reservoir may define a volume and may be configurable between an empty state and a full state. When in the empty state, the expandable reservoir may contain no therapeutic fluid, and when in the full state, the expandable reservoir may be full of therapeutic fluid. The expandable reservoir may include a movable wall that moves in response to the expansion and contraction of the expandable reservoir between the empty state and the full state. The device may further include one or more light-based volume sensors located in the housing to sense one or more light signals representative of a distance between the one or more volume sensors and the movable wall of the expandable reservoir to determine the volume of the expandable reservoir.

In one or more embodiments, the housing may include a bulkhead partitioning an interior space of the housing to define a reservoir chamber, and the expandable reservoir may be located in the reservoir chamber and the one or more light-based volume sensors may be located outside of the reservoir chamber.

In one or more embodiments, the one or more light-based volume sensors may transmit and receive light to and from the movable wall through the therapeutic fluid contained in the expandable reservoir. In one or more embodiments, the one or more light-based volume sensors may be spaced away from the expandable reservoir defining space therebetween.

In one or more embodiments, the housing may further include a window portion defining at least a portion of the expandable reservoir, and the one or more light-based volume sensors may transmit and receive light into and out of the expandable reservoir through the window portion. The window portion may include (e.g., be at least partially formed of) sapphire.

In one or more embodiments, the device or system may further include a computing apparatus operably coupled to the one or more light-based volume sensors to receive data corresponding to the one or more light signals representative of the distance between the one or more light-based volume sensors and the movable wall of the expandable reservoir and to determine the volume of the expandable reservoir based on the data corresponding to the one or more light signals. In one or more embodiments, the device may further include telemetry apparatus to wirelessly transmit data representative of the volume of the expandable reservoir to an external device.

One exemplary implantable therapeutic pump may include an expandable reservoir to contain therapeutic fluid. The expandable reservoir may define a volume and may be configurable between an empty state and a full state. When in the empty state, the expandable reservoir may contain no therapeutic fluid, and when in the full state, the expandable reservoir may be full of therapeutic fluid. The expandable reservoir may include a movable wall that moves in response to the expansion and contraction of the expandable reservoir between the empty state and the full state. The pump may further include one or more volume sensors (e.g., a light-based sensor where the signal is a light signal such as infrared, a sound-based sensor where the signal is a sound signal such as ultrasound) to transmit one or more signals to the movable wall of the expandable reservoir through the therapeutic fluid contained in the expandable reservoir and to receive the one or more signals reflected from the movable wall of the expandable reservoir to determine a volume of the expandable reservoir.

An exemplary infusion system may include a housing and an expandable reservoir located in the housing to contain therapeutic fluid. The expandable reservoir may define a volume and may be configurable between an empty state and a full state. When in the empty state, the expandable reservoir may contain no therapeutic fluid, and when in the full state, the expandable reservoir may be full of therapeutic fluid. The expandable reservoir may include a movable wall that moves in response to the expansion and contraction of the expandable reservoir between the empty state and the full state. The system may further include one or more sensors located in the housing to sense one or more signals representative of a distance between the one or more sensors and the movable wall of the expandable reservoir. The system may further include computing apparatus operably coupled to the one or more sensors to determine the volume of the expandable reservoir based on the one or more signals representative of a distance between the one or more sensors and the movable wall of the expandable reservoir. In one or more embodiments, the computing apparatus may be located in the housing. In one or more embodiments, the system may further include an external device, and the computing apparatus may be located in the external device and is operably coupled to the one or more sensors wirelessly.

In one or more embodiments, propellant is disposed in the reservoir chamber outside of the expandable reservoir to exert pressure on at least a portion of the expandable reservoir. In one or more embodiments, the reservoir may include a fixed wall opposite the movable wall, and the fixed wall may be in a fixed position with respect to the one or more volume sensors. The one or more volume sensors may transmit and receive the one or more signals to determine a distance between the fixed wall and the movable wall.

One or more exemplary implantable infusion devices may include a light-based volume sensor. The light-based volume sensor may include, or utilize, an infrared emitter/detector, which may be housed in the bulkhead, preferably mounted to the underside of the pump hybrid of the infusion device. The exemplary device may further include a hermetic window placed, or positioned, in alignment with the sensor at a specified distance to allow the light to emit towards an end terminal, or movable wall, of a bellows-style reservoir from an infrared emitter. The position of the end terminal, or movable wall, of the bellows-style reservoir with respect to the light-based volume sensor may be a function of the volume of fluid in the bellows. In at least one embodiment, the implantable infusion devices may include or incorporate the use of, a bellows-style reservoir that defines a light-reflective surface that moves correspondingly with the reservoir fill level.

One or more exemplary methods may be described as accurately measuring the fill level, or volume, of therapeutic fluid, or drug, within a reservoir. The exemplary methods may use a light-emitting diode (LED), such as an infrared LED, to reflect light off a rigid surface or another object of a bellows-style reservoir as it moves with, or in response to, the reservoir volume changes. This reflected light may then be sensed by a photodiode or phototransistor and may be used to compute the distance between the sensor and the rigid surface or another object. As the bellows-style reservoir compresses, the rigid surface or another object may move with respect to the reservoir volume changes, and a voltage or current signal sensed by the photodiode or phototransistor may be proportional to the distance the rigid surface or another object moved, which can be provided to an electronic control interface, such as a circuit in an implantable infusion device. The exemplary method may then provide an alert to a user, e.g., using the electronic control interface, when the reservoir is nearing empty. In one or more embodiments, the LED and the photo receiver device may operate through a hermetically-sealable window configured to transmit the appropriate wavelengths of light therethrough. The hermetically-sealable window may include one or more materials such as glass, sapphire, and polymer.

Further, the exemplary method may also use the reservoir fill level as a flow meter for the pumping device as each incremental change in reservoir volume as pump strokes/ pulses are sensed. Such flow meter information may be used to correct for inaccuracies that may result from uncontrollable variations.

The above summary is not intended to describe each embodiment or every implementation of the present disclosure. A more complete understanding will become apparent and appreciated by referring to the following detailed description and claims taken in conjunction with the accompanying drawings.

DETAILED DESCRIPTION

Figure 1:
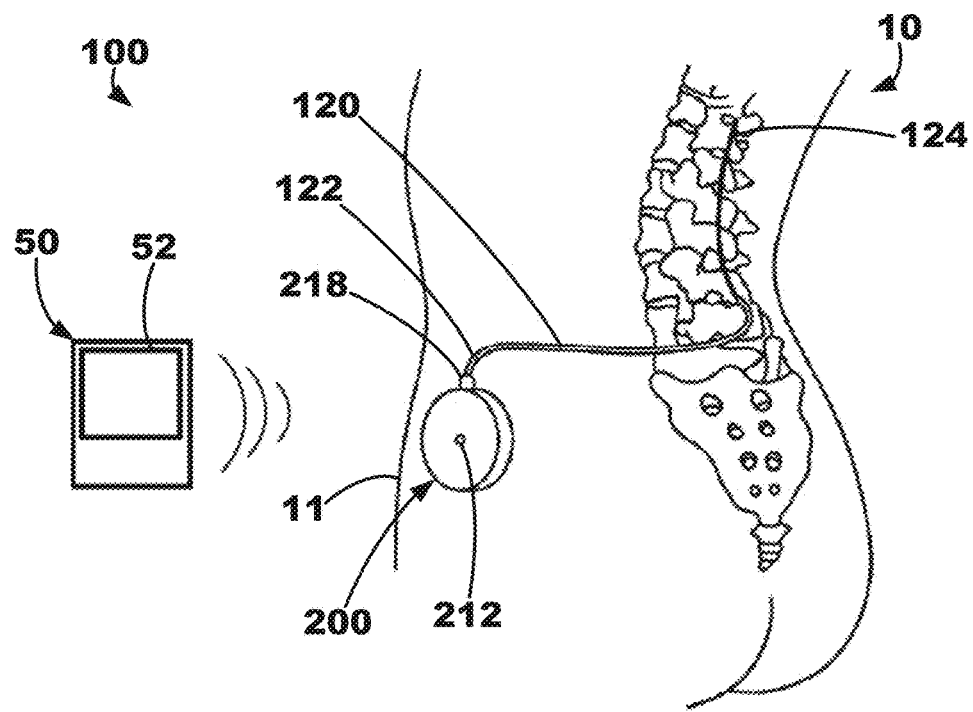
FIG. 1 is schematic view showing an exemplary infusion system including an implantable infusion device implanted in a patient and an external device.

Exemplary systems, devices, apparatus, and methods shall be described with reference to FIGS. 1-6. It will be apparent to one skilled in the art that elements or processes from one embodiment may be used in combination with elements or processes of the other embodiments, and that the possible embodiments of such systems, devices, apparatus, and methods using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise. As used herein, "have," "having," "include," "including," "comprise," "comprising" or the like are used in their open ended sense, and generally mean "including, but not limited to."

As used herein, "full," or the like, as it relates to a reservoir volume means a volume to which the reservoir is intended to be filled, and does not necessarily, and often does not, refer to the maximum volume of fluid that the reservoir can contain. For example, a 20 ml reservoir in an implantable infusion device may contain 22 ml or more of fluid. However, for the purposes of device and therapy reliability, it is often desired or intended for the reservoir to be refilled to a volume of 20 ml. Thus, the intended volume of 20 ml of such a device would be the full volume for the purposes of this disclosure. Regardless of the intended volume of the reservoir, it will be understood that "full" may include +/−5% of the intended full volume, as manufacturing variability and other design and use constraints often make it difficult or impracticable to precisely make each device perform identically with regard to reservoir full status. "Full" may refer to the point at which a wall or surface of a collapsible member defining the reservoir contacts a lower, or far, interior surface of a reservoir chamber. Conversely, as used herein, "empty," or the like, as it relates to a reservoir volume means a volume to which the reservoir is effectively empty such that fluid contain therein may not be able to be effectively used by the remainder of the device or system, and does not necessarily, and often does not, refer to absolutely zero amount of fluid in the reservoir. Further, empty may refer to the point at which a wall or surface of a collapsible member defining the reservoir contacts an upper, or near, interior surface of a reservoir chamber (e.g., at the bulkhead).

Any direction referred to herein, such as "top," "bottom," "left," "right," "upper," "lower," and other directions or orientations are described herein for clarity in reference to the figures and are not intended to be limiting of an actual device or system. Devices and systems described herein may be used in a number of directions and orientations.

The exemplary systems, devices, apparatus, and methods may include, or use, at least one volume sensor to measure the volume of a reservoir. The reservoir may be part of, or included within, an implantable infusion device to deliver therapeutic fluid, or a drug, to a patient within which the implantable infusion device may be implanted.

Although the exemplary systems, apparatus, devices, and methods described herein may be employed with or by any suitable implantable infusion system, an exemplary system 100 that includes an implantable infusion device 200 that includes, or uses, at least one volume sensor to measure a volume of a reservoir is depicted in FIG. 1. The exemplary system 100 includes an implantable infusion device 200 and a catheter 120. The catheter 120 is operably coupled to the infusion device 200 such that the catheter 120 is in fluid communication with a reservoir (not shown in FIG. 1) of the device 200.

The depicted implantable infusion device 200 includes a fill, or refill, port 212 in communication with the reservoir, which is disposed within the housing of the device 200. The supply of therapeutic fluid, or agent, in the reservoir may be replenished via the fill port 212. The implantable infusion device 200 may include any suitable mechanism or structure capable of delivering one or more fluids, or drugs, to a patient 10. The structures used to drive fluids in the implantable infusion device 200 may be powered (e.g., piston pumps, diaphragm pumps, peristaltic pumps, etc.), may be activated based on pressure to drive fluid out of a reservoir (e.g., using collapsing diaphragms, expanding bladders, osmotic, etc.), and/or combinations thereof. The implantable infusion device 200 may include, or contain, a catheter access port 218 in communication with the catheter 120 at a location upstream of the reservoir.

The implantable infusion device 200 depicted in FIG. 1 is shown implanted in a patient 10. The proximal end 122 of the catheter 120 is coupled to the catheter access port 218 of the implantable infusion device 200. The implantable infusion device 200 may be surgically implanted in any suitable location, such as subcutaneously in the pectoral, abdominal, or other region of the body of the patient 10. The distal end 124 of the catheter 120 may be implanted in a patient 10 such that the distal end 124 is located at a selected internal delivery, or target, site in the patient 10. For example, the distal end 124 of the catheter 120 is implanted in the intrathecal space of the patient 10 in FIG. 1. In other embodiments, the distal end 124 of the catheter 120 is implanted in the cerebroventricles, or elsewhere as desired.

The exemplary system 100 further includes an external device 50 capable of wireless communication, or telemetry, with the implantable infusion device 200. The external device 50 may include a display 52 for presenting information to a user, such as a healthcare provider or patient. In one or more embodiments, the external device 50 is capable of presenting volume information, using the display 52 and/or another output device, to the user regarding the amount, or volume, of the therapeutic fluid, or drug, remaining, or located within, the reservoir of the implantable infusion device 200. In one or more embodiments, the external device 50 is capable of presenting alerts, or notifications, using the display 52 and/or another output device, to the user to indicate to the user that the amount, or volume, of the therapeutic fluid, or drug, remaining, or located within, the reservoir of the therapeutic infusion device 200 has reached a selected, or particular, limit. For example, the external device 50 may provide any alert, or notification, to a user when the reservoir contains less than a selected number, or amount, of prescribed therapeutic fluid doses or deliveries (e.g., less than 50 prescribed doses of therapeutic fluid, less than 10 prescribed doses of therapeutic fluid, etc.). Further, for example, the external device 50 may provide any alert, or notification, to a user when the reservoir contains less than a selected time period of prescribed therapeutic fluid deliveries (e.g., less than a month left of prescribed doses of therapeutic fluid, less than a week left of prescribed doses of therapeutic fluid, etc.).

Any suitable external device 50, such as a programmer (e.g., a MEDTRONIC, INC. N'VISION clinician programmer or a MEDTRONIC, INC. MYP™ patient programmer), a tablet computer, a smart phone, a personal data assistant, a laptop computer, or the like, may be employed, provided that it can communicate with the implantable infusion device 200. In one or more embodiments, the external device 50 is a cellular telephone and the display 52 is the touchscreen, or screen, of the cellular telephone. In one or more embodiments, the external device 50 is a desktop computer with an associated monitor serving as the display 52.

The external device 50 may include a telemetry circuit and an antenna for bidirectional communication with the implantable infusion device 200. Data and commands may be transmitted and received during uplink or downlink telemetry between the implantable infusion device 200 and the external device 50 using the telemetry circuit and the antenna. In at least one embodiment, the wireless operable coupling between the implantable infusion device 200 and the external device 50 may use one or more wireless (e.g., radio frequency) data transmission protocols such as, e.g., BLUETOOTH, WI-FI, Medical Implant Communications Service (MICS), any protocol in the ultra-high frequency (UHF) band, any protocol in the super high frequency (SHF) band, low frequencies, etc.

Further, the external device 50 may be described as being a microprocessor-controlled device, and thus, may include computing apparatus that includes one or more microprocessors that operate with associated memory for controlling various processes and functions of the external device 50 including initiating one or more volume measurements using the implantable infusion device 200, wirelessly transferring data and commands between the implantable infusion device 200 and the external device 50, issuing alerts, or notifications based on volume measurements of the reservoir of the implantable infusion device 200, calculating a volume of the reservoir of the implantable infusion device 200 based on various electrical signals and/or times from one or more sensor devices and apparatus, etc. Still further, the external device 50 may be further configured to store data from the implantable infusion device 200 such as, e.g., reservoir volume data over time, average flow rates, sensor system diagnostics, volume discrepancies (e.g. with respect to programmed expectations) for various time durations, events where volume changes exceed selected thresholds, etc.

In order for a person to interact with the external device 50, the external device 50 may include a user interface coupled to the computing apparatus. The user interface may include a touchscreen, a keyboard, graphical user interface, and/or combinations thereof. For example, the display 52 may be touchscreen that may allow a user to view and/or manipulate data on the display 52 and allow a user to interact with the implantable infusion device 200. The external device 50 may further include a speaker for broadcasting audible tones or messages used to communicate with a user regarding, e.g., vocalizations of volumes, alerts, alarms, notifications, etc. The external device 50 may further include a communications module or other functionality used for transferring data (e.g., over the internet, over a network, etc.) to a central database or communicating with patient management systems.

Figure 2:
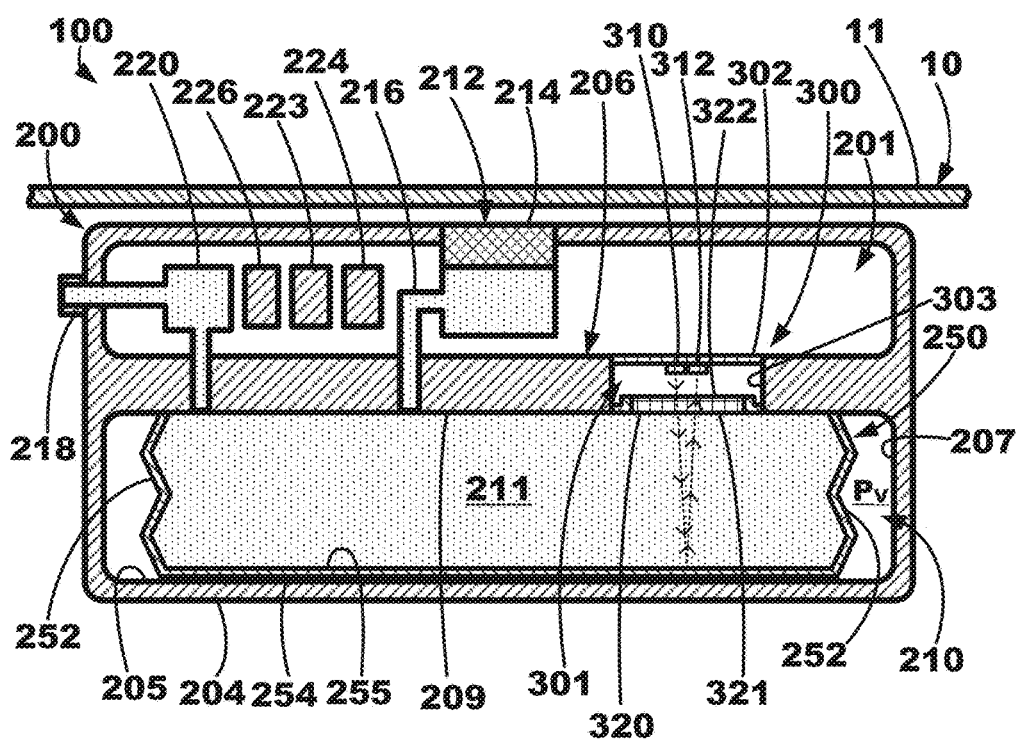
FIG. 2 is a schematic cross-sectional view of an exemplary implantable infusion device such as shown in FIG. 1 including a light-based volume sensor and a "full" reservoir.
Figure 3:
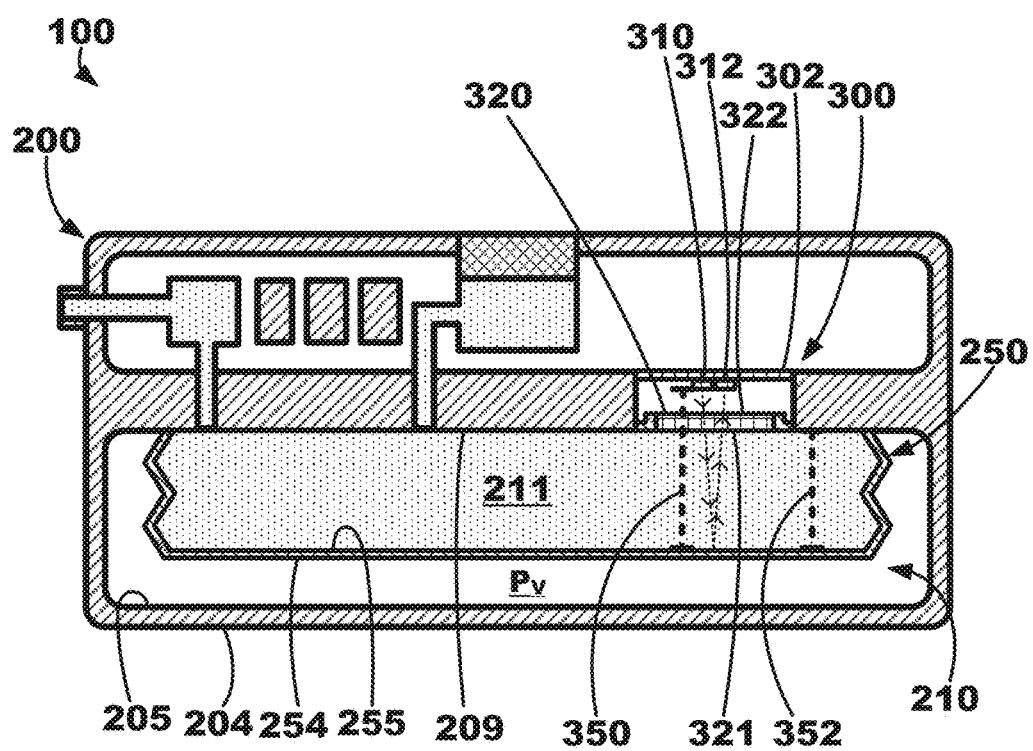
FIG. 3 is another schematic cross-sectional view of the implantable infusion device of FIG. 2 with the reservoir about ⅔ "full."
Figure 4:
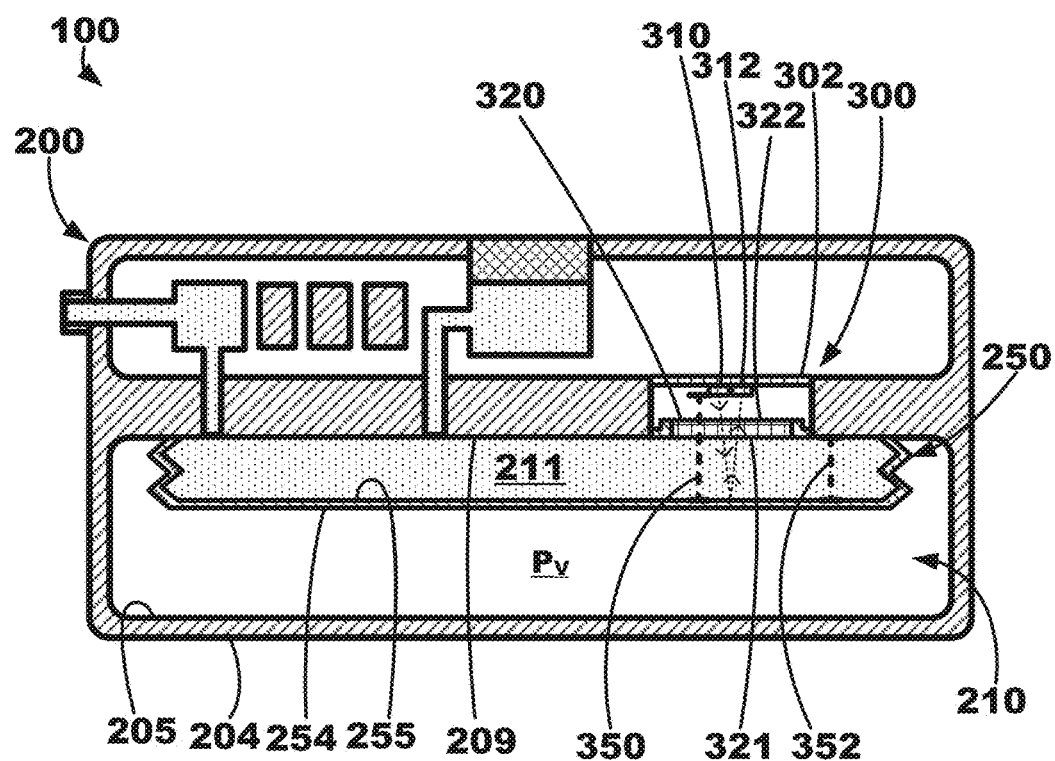
FIG. 4 is another schematic cross-sectional view of the implantable infusion device of FIGS. 2-3 with the reservoir about ⅓ "full."

The implantable infusion device 200 of FIG. 1 is depicted cross-sectionally in FIGS. 2-4 with the reservoir therein configured in various states of "full"-ness. As shown in FIG. 2, the implantable infusion device 200 may be implanted underneath and close to the skin 11 of the patient 10. The device 200 may include a housing 204 with a bulkhead 206 that divides an interior space 201, of the housing 204 into two or more chambers. For example, as shown, the interior space 201 of the housing 204 may include a reservoir chamber 210 that is at least partially defined by the bulkhead 206. More specifically, reservoir chamber 210 may be defined by a lower, or far, interior surface 205, a cylindrical side interior surface 207, and an upper, or near, interior surface 209. As shown in this embodiment, the lower, or far, interior surface 205 and the cylindrical side interior surface 207 may be defined by one or more portions, or walls, of the housing 204, and the upper, or near, interior surface 209 may be defined by one or more portions of the bulkhead 206 as well as other components as described further herein. The bulkhead 206 may serve to isolate a reservoir within the reservoir chamber 210 from other selected components of the implantable infusion device 200, such as computing apparatus, telemetry circuitry, etc. More specifically, the reservoir chamber 210 and the reservoir contained therein may be hermetically-sealed from the remainder of the implantable infusion device 200.

The implantable infusion device 200 may further include an expandable reservoir 250 located in the hermetically-sealed space of the reservoir chamber 210 and configured to hold therapeutic fluid 211 therein. Generally, the expandable reservoir 250 may define a hermitically-sealed container, or receptacle, for holding, or containing, therapeutic fluid 211. The volume of the reservoir 250 holding, or containing, therapeutic fluid 211 may change based on how much of the therapeutic fluid 211 is located therein.

The expandable reservoir 250, at least in the illustrated embodiment, may be a collapsible bellows-style reservoir that includes at least a cylindrical side wall 252 and a movable wall 254. In this embodiment, the expandable reservoir 250 may be sealed against the upper, or near, interior surface 209 of the bulkhead 206 such that the upper, or near, interior surface 209 of the bulkhead defines an interior surface of the reservoir 250. It will be understood, however, that reservoirs other than bellows-type reservoirs may not be attached and sealed against the upper interior surface 209 of the reservoir chamber 210, and in some embodiments, a bulkhead 206 may not be utilized. Further, it will be understood that any type of collapsible reservoir, such as an expandable and collapsible bag, an elastomeric balloon-type reservoir, or the like, may be employed using the exemplary systems, apparatus, devices, and methods described herein.

The movable wall 254 of the reservoir 250 may be described as being rigid, or resilient, so as to be resistant to deflection. For example, in this embodiment, the movable wall 254 may lie in plane, or be planar, and may resist deflection out of the plane. As such, the movable wall 254 may move as a single element, e.g., towards and away from the lower, or far, interior surface 205 of the reservoir chamber 250, and towards and away from the upper, or near, interior surface 207 of the reservoir chamber 250. More specifically, the movable wall 254 may be described as moving substantially linearly along an axis that is perpendicular to the plane of the movable wall. In other words, the moveable wall 254 may be described as moving orthogonally to the plane that the moveable wall 254 lies within.

The movable wall 254 may move between a "full" state, or position, as shown in FIG. 2 and an "empty" state, or position in response to changes in volume of therapeutic fluid, or drug, 211 contained in the reservoir 250. More specifically, when the expandable reservoir 250 is in a "full" state, the expandable reservoir 250 may be expanded (e.g., stretched, spread, unfurled, etc.) to a maximum volume or capacity (e.g., so as to hold, or contain, a maximum amount or volume of therapeutic fluid 211), and when the expandable reservoir 250 is in a "empty" state, the expandable reservoir 250 may be collapsed (e.g., compressed, contracted, deflated, etc.) to a minimum volume or capacity (e.g., so as to hold, or contain, no or a minimum amount or volume of therapeutic fluid). When in the full state, the movable wall 254 may be positioned a maximum distance away from the upper interior surface 209 of the reservoir chamber 210 or the bulkhead 206. In some embodiments, the movable wall 254 may be positioned proximate, or adjacent, to the lower, or far, interior surface 205 of the reservoir chamber 210 when in the full state. When in the empty state, the movable wall 254 may be positioned a minimum distance away from the upper interior surface 209 of the reservoir chamber 210 or the bulkhead 206. Further, in some embodiments, the movable wall 254 may be positioned proximate, or adjacent, to the upper, or near, interior surface 209 of the reservoir chamber 210 when in the empty state.

The reservoir chamber 210 may further include a propellant, or propellant mixture, $P_V$ disposed outside of the reservoir 250 but inside the reservoir chamber 210 so as to at least partially surround the reservoir 250. The propellant $P_V$ can exert a pressure on at least a portion of the expandable reservoir 250 such that the pressure in the reservoir 250 is positive. Further, when therapeutic fluid 211 is removed from the reservoir 250 (e.g., to delivered to the patient, to be removed from the pump by a clinician, etc.), the pressure exerted on the reservoir 250 by the propellant $P_V$ may assist in fluid exit from the reservoir 250. More specifically, the reservoir 250 may contract due to the therapeutic fluid 211 exiting the reservoir 250 and the pressure exerted on the exterior of the reservoir 250 by the propellant $P_V$.

The device 200 may further include a fill port 212 through which a needle of a refill kit, may enter to refill the reservoir 250. The fill port 212 may include a self-sealing, needle-penetrable septum 214. The fill port 212 may be coupled to the reservoir 250 via, for example, a refill passageway 216. In addition to the fill port 212, the device 200 may include a catheter access, or outlet, port 218 for delivering the therapeutic fluid 211 to the catheter 120, and in turn, to the patient 10 as shown in FIG. 1. The therapeutic fluid 211 may be transferred from the reservoir 250 to the catheter access port 218 via a pumping mechanism, apparatus, 220, such as a piston pump or peristaltic pump or through any other mechanism or technique.

The implantable infusion device 200 may include other components such as computing apparatus 226, a telemetry circuit 223, and a power source 224 to power such apparatus and circuits as well as the remainder of the device 200. The computing apparatus 226 may include one or more microprocessors that operate with associated memory for controlling various processes and functions of the implantable infusion device 200. The telemetry circuitry 223 may include an antenna, and may be configured to be used with the computing apparatus 226 to transmit and receive data and commands during uplink or downlink telemetry between the device 200 and the external device 50. In at least one embodiment, the wireless operable coupling between the implantable infusion device 200 and the external device 50 may use one or more wireless (e.g., radio frequency) data transmission protocols such as, e.g., BLUETOOTH, WI-FI, Medical Implant Communications Service (MICS), any protocol in the ultra-high frequency (UHF) band, any protocol in the super high frequency (SHF) band, low frequencies, etc.

The exemplary implantable infusion device 200 may further include a volume sensor 300 to determine the volume of the reservoir 250. Although this embodiment depicted in FIGS. 2-4 includes a single sensor 300, exemplary systems, devices, and pumps may include more than a single sensor such as a plurality of sensors (e.g., two or more volume sensors, three or more volume sensors, a plurality of volume sensors, etc.). To determine the volume of the reservoir 250, the volume sensor 300 may be generally described as being able to determine the position of the movable wall 254 of the expandable reservoir 250, which may be used to determine the volume of the expandable reservoir 250. For example, the volume sensor may transmit a signal (e.g., an electromagnetic signal, a light signal, an infrared signal a sound signal, an ultrasound signal, etc.) as represented by a dotted line arrow in FIG. 2 to the movable wall 254 of the reservoir 250. The signal may be reflected from the movable wall 254, or more specifically, the interior surface 255 of the movable wall 254, and the volume sensor 300 may receive the reflected signal. One or more properties of the reflected signal may be used to determine, or calculate, the volume of the reservoir as will be described further herein.

Nonetheless, the reflected signal, or properties with respect thereto or thereof, may be geometrically related to, or representative of, a distance 350 labeled in FIGS. 3-4 between the volume sensor 300 and the movable wall 254. As such, the signal may be used to may be used to determine the distance 350 between the volume sensor 300 and the movable wall 254. The volume sensor 300 may be operably coupled (e.g., electrically connected) to the computing apparatus 226 to provide data regarding the signal (e.g., voltage, current, impedance, noise, timing information such as duty cycle and pulse amplitude, intensity, etc.), such that the computing apparatus 226 can initiate a volume measurement, etc. and to the power source 224 to provide electricity thereto.

More specifically, in at least one embodiment including a single volume sensor 300, the distance 350 between the volume sensor 300 and the movable wall 254 may be used to determine the volume of the reservoir since, e.g., the movable wall 254 is rigid and moves orthogonally to the plane it lies within. For example, assuming that the reservoir is generally shaped as a cylinder and the radius of the cylinder is known, the distance 350 may represent at least portion of the height of the cylinder-shaped reservoir 250, which may be used to compute the volume of the reservoir 250 using the geometric properties of a cylinder. In other embodiments including multiple volume sensors, the multiple volume sensors may be located in different locations to measure various distances of the reservoir (e.g., between various walls, surfaces, etc.), which may be used to compute the volume of the reservoir using appropriate mathematical properties.

Geometrically, as shown in FIGS. 3-4, the distance 350 between the volume sensor 300 and the movable wall 254 may not represent the height of the reservoir 250 because, for example, the volume sensor 300 may be located a fixed distance away from the upper interior surface 209 of the reservoir chamber 210, which also defines a fixed wall of the reservoir 250. Thus, the fixed distance that the volume sensor 300 is located away from the interior surface 209 of the reservoir chamber 210 may be subtracted from the distance 350 to obtain the height 352 of the reservoir 250. In other words, the volume sensor 300 may be spaced away from the interior surface 209 of the reservoir chamber 210 to define a space (e.g., an air gap). In at least one embodiment, the volume sensor 300 may be mounted about 3.5 millimeters (mm) from the upper interior surface 209 of the reservoir chamber 210 defined by the bulkhead 206.

Figure 5:
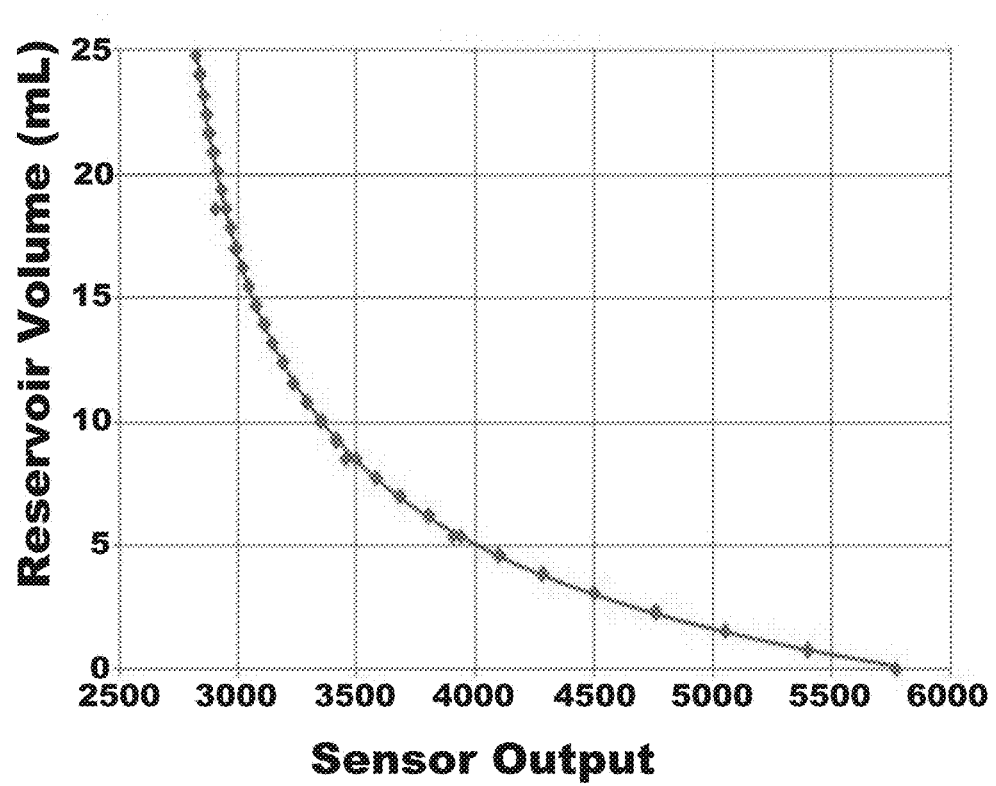
FIG. 5 is a graph of volume sensor output versus reservoir volume.

Regardless, the distance measured, or determined, by the volume sensor 300 between the volume sensor 300 and the moveable wall 254 may be calibrated, or normalized, to the volume of the reservoir 250 through a functional, or mathematical, relationship. For example, a graph of volume sensor output versus reservoir volume is depicted in FIG. 5. As shown, a volume sensor output may be calibrated to a reservoir volume, and a function may be defined thereby such that, e.g., the volume of the reservoir 250 may be determined based solely on the volume sensor's output (e.g., a quantitative proximately value). In this example, about 4000 units corresponds to about 5 mL of therapeutic fluid 211 in the reservoir 250, and about 3000 units corresponds to about 16 ml of therapeutic fluid 211 in the reservoir 250. The volume sensor 300 may be sensitive to volume changes between about 0.1 ml to about 1 ml. In at least one embodiment, the volume sensor 300 may be sensitive to volume changes less than or equal to about 0.45 ml.

The signal transmitted and received by the volume sensor 300 may be a light signal, and thus, the volume sensor 300 may be referred to as a light-based sensor. For example, and more specifically, the volume sensor 300 may include a light source 310 (e.g., emitter, transmitter, etc.) to emit, or transmit, light through the reservoir 250 to the movable wall 254 and a light receiver 312 (e.g., detector, etc.) to detect the light reflected from the movable wall 254. The light source 310 may be include one or more of a light emitting diode, a laser, an infrared source such as an infrared emitting diode (IRED), etc. The light source 310 may be configure to generate, or emit, light having one or more wavelengths between about 350 nanometers (nm) and about 50,000 nm. In at least one embodiment, the light source 310 is an infrared source such as an infrared light emitting diode. Further, the light source 310 may include a current source having an emitter current between bout 1 mA and about 500 mA. For example, computed 3-standard deviation volume estimation error limits were ±0.58 ml and ±0.45 ml for 10 mA and 200 mA emitter currents, respectively.

The light receiver, or detector, 312 may be generally described as any apparatus configured to generate a signal (e.g., an analog or digital electrical signal to be used by computing apparatus, etc.) in response to reception of the reflected light from the movable wall 254 that is usable for volume determine as described herein. The light detector 312 may include one or more of a photodiode, a phototransistor, an avalanche diode, a photoelectric sensor, a micromechanical system (MEMS), a resonator, etc.

The volume sensor 300 in this embodiment may be located within a cavity 301 within, or defined by, the bulkhead 206. The cavity 301 may be separate from the reservoir chamber 210, and thus, the volume sensor 300 may be described as being located outside of the reservoir chamber 210. In other words, the volume sensor 300 may be not be located within the reservoir chamber 210 or the reservoir 250 so as to maintain the hermetically-sealed properties of both of the reservoir chamber 210 and the reservoir 250. The cavity 301 may be defined by a sidewall 303, a window 320, and the volume sensor 300 mounted on, or coupled, to a substrate element 302. The substrate 302 may be a printed circuit board (PCB) including, or at least operably coupled to, one or more integrated circuits and electronic components such as, e.g., the computing apparatus 226, the telemetry circuit 223, and the power source 224.

The volume sensor 300 may be fixedly coupled to the substrate element 302, which is fixedly coupled to the bulkhead 206. Thus, the volume sensor 300 may be in a fixed, or unmovable, relationship with respect to the bulkhead 206. Since the bulkhead 206 defines the upper, or near, interior surface 209 of reservoir chamber 210, which also defines an interior surface of the reservoir 250, it may be described that the reservoir 250 includes a fixed wall, or surface, 209 opposite the movable wall 254 and the fixed wall 209 is in a fixed position with respect to the volume sensor 300.

The window 320 may be light transmissive to receive and transmit at least a portion of the light transmitted from the light source 310 into the reservoir 250 to the moveable wall 254, and to receive and transmit at least a portion of reflected light from the moveable wall 254 and the cavity 301 to the light receiver 312. The window 320 may define at least a portion of the upper, or near, interior surface 209 of the reservoir chamber 210, and in this embodiment, an interior surface of the reservoir 250. Thus, the volume sensor 300 may be described as capable of transmitting a signal through the fixed wall 209 using the window 320 or other apparatus having similar functionality, and through the therapeutic fluid 211 to the movable wall 254. Conversely, the volume sensor 300 may be described as capable of receiving a signal reflected from the movable wall 254 through the therapeutic fluid 211 and through the fixed wall 209 using the window 320 or other apparatus having similar functionality.

The window 320 may define a first surface 321 facing the interior of the reservoir chamber 210 and the interior of the reservoir 250 and an opposite second surface 322 facing away from the reservoir chamber 210 and into the cavity 301 and volume sensor 300. The window 320 may define a thickness between the first surface 321 and the second surface 322 that may be between about 1 millimeter (mm) and about 3 mm. In at least one embodiment, the thickness may be about 1.5 mm. The window 320 may include one or more light transmissive materials such as, e.g., sapphire, glass, polymer, fused silica, borosilicate, germanium, magnesium fluoride, etc. In essence, the window 320 may include any one or more materials so as to be capable of at least transmitting the signal, such as light signal, transmitted and received by the volume sensor 300 therethrough.

The reservoir 250 is in a full state as shown in FIG. 2. Thus, the volume sensor 300 may transmit a light signal (as represented by dashed line arrows) from the light source 310 through the cavity 301, through the window 320 into the reservoir 250, through the therapeutic fluid 211 in the reservoir 250, and to the interior surface 255 (which may be at least partially reflective) of the movable wall 254. The light signal (as represented by dashed line arrows) may be reflected from the interior surface 255 of the movable wall 254 through the therapeutic fluid 211, through the window 320, and through the cavity 301 to the light receiver 312. The measured signal may be used to determine the volume of the reservoir 250, for example, using the relationship depicted in FIG. 5. Since the reservoir 250 is full in FIG. 2, it would be expected that the light receiver 312 would return a value of about 2850 units (see FIG. 5) based on a 20 ml reservoir.

The reservoir 250 is in a ⅔ full state and a ⅓ full state in FIGS. 3-4, respectfully. As a result, it would be expected that the light receiver 312 would return a value of about 3100 units (see FIG. 5) based on a 20 ml reservoir for the ⅔ full state in FIG. 3 and a value of about 3650 units based on a 20 ml reservoir for the ⅓ full state in FIG. 4.

Although the example depicted in FIGS. 2-4 utilizes a light-based modality such as infrared, it is to be understood that the exemplary systems, apparatus, devices, and methods described herein may use various modalities of sensing and detection to determine the volume of a reservoir 250 of an implantable infusion device 200. For example, an exemplary system 100 and device 200 may include a volume sensor 400 that utilizes sound, e.g., ultrasound, as depicted in FIG. 6.

Figure 6:
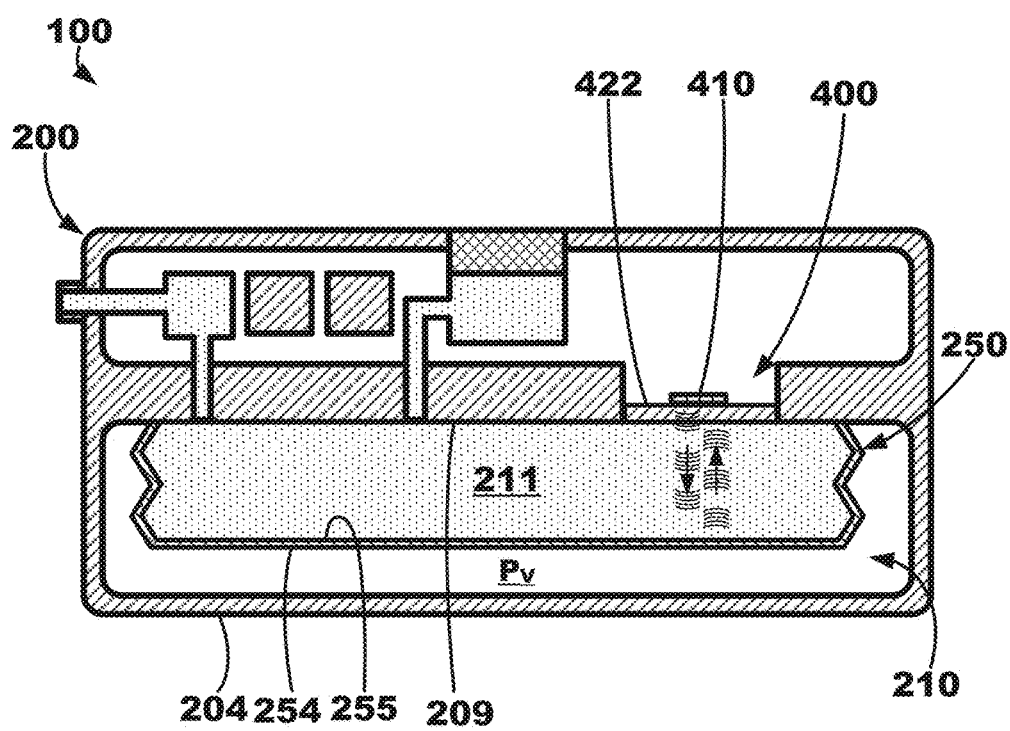
FIG. 6 is a schematic cross-sectional view of an exemplary implantable infusion device such as shown in FIG. 1 including a sound-based volume sensor and a ⅔ "full" reservoir.

The volume sensor 400 of FIG. 6 may include a single ultrasound transducer 410 configured to transmit and receive ultrasound signals to and from the movable wall 254 (and more specifically, the interior surface 255 of the movable wall 254, which may be at least partially reflective) to determine a distance between the movable wall 254 and the volume sensor 400. The volume sensor 400 may be located adjacent ultrasound-conductive material portion 422, which may be part of the bulkhead 206. In other embodiments, the volume sensor 400 may include a separate ultrasound transmitter and receiver. In one or more other embodiments, the volume sensor 400 may include a plurality of ultrasound sensors using one or more different wavelengths to, e.g., account for differences in fluids, which may have different absorption properties.

Although the exemplary systems depicted and primarily described herein utilizes either light or ultrasound modalities, it is to be understood that exemplary systems may also use other sensing modalities and corresponding apparatus to measure positioning of one or more portions of the reservoir to estimate volume. For example, other exemplary systems may utilize changes in resistance such as, e.g., using a strain sensor, may utilize changes in inductance such as, e.g., using a wire coil in proximity with another coil or as it deforms, may utilize changes in capacitance where positioning of parallel plates may cause a change in measured capacitance, may utilize changes in magnetic fields, or utilize changes in a piezoelectric charge generated in response to mechanical changes. Additionally, sensing may occur at one site on the reservoir, or may be performed at multiple sites on the reservoir to improve estimates. Additionally, sensing sites may include the interior or the exterior of the reservoir.

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the systems, devices, apparatus, and methods described herein. Various modifications of the illustrative embodiments, as well as additional embodiments of the disclosure, will be apparent upon reference to this description.

What is claimed is:

1. An implantable medical infusion device comprising:
   a housing;
   an expandable reservoir located in the housing to contain therapeutic fluid, wherein the expandable reservoir defines a volume and is configurable between an empty state and a full state, wherein the expandable reservoir comprises a movable wall that moves in response to the expansion and contraction of the expandable reservoir between the empty state and the full state; and
   a light-based volume sensor located in the housing to sense a light signal representative of a distance between the volume sensor and the movable wall of the expandable reservoir to determine the volume of the expandable reservoir, wherein the light-based volume sensor transmits and receives light to and from the movable wall through the volume of the expandable reservoir.

2. The device of claim 1, wherein the housing comprises a bulkhead partitioning an interior space of the housing to define a reservoir chamber, wherein the expandable reservoir is located in the reservoir chamber, wherein the light-based volume sensor is located outside of the reservoir chamber.

3. The device of claim 1, wherein the light-based volume sensor transmits and receives light to and from the movable wall through the therapeutic fluid contained in the expandable reservoir.

4. The device of claim 1, wherein the housing further comprises a window portion defining at least a portion of the expandable reservoir, wherein the light-based volume sensor transmits and receives light into and out of the expandable reservoir through the window portion.

5. The device of claim 4, wherein the window portion comprises sapphire.

6. The device of claim 1, wherein the light-based volume sensor is spaced away from the expandable reservoir defining space therebetween.

7. The device of claim 1, further comprising a computing apparatus operably coupled to the light-based volume sensor to receive data corresponding to the light signal representative of the distance between the volume sensor and the movable wall of the expandable reservoir and to determine the volume of the expandable reservoir based on the data corresponding to the light signal.

8. The device of claim 1, further comprising telemetry apparatus to wirelessly transmit data representative of the volume of the expandable reservoir to an external device.

9. An implantable therapeutic pump comprising:
an expandable reservoir to contain therapeutic fluid, wherein the expandable reservoir defines a volume and is configurable between an empty state and a full state, wherein the expandable reservoir comprises a movable wall that moves in response to the expansion and contraction of the expandable reservoir between the empty state and the full state; and
a volume sensor to transmit a signal to the movable wall of the expandable reservoir through the therapeutic fluid contained in the expandable reservoir and to receive the signal reflected from the movable wall of the expandable reservoir to determine a volume of the expandable reservoir.

10. The pump of claim 9, wherein volume sensor is a light-based sensor and the signal is a light signal.

11. The pump of claim 9, wherein volume sensor is a sound-based sensor and the signal is a sound signal.

12. The pump of claim 9, further comprising a housing defining an interior space, wherein the housing comprises a bulkhead partitioning the interior space of the housing to define a reservoir chamber, wherein the expandable reservoir is located in the reservoir chamber, wherein the volume sensor is located outside of the reservoir chamber.

13. The pump of claim 12, further comprising a propellant disposed in the reservoir chamber outside of the expandable reservoir to exert pressure on at least a portion of the expandable reservoir.

14. The pump of claim 9, wherein the reservoir comprises a fixed wall opposite the movable wall, wherein the fixed wall is in a fixed position with respect to the volume sensor, wherein the volume sensor transmits and receives the signal to determine a distance between the fixed wall and the movable wall.

15. An infusion system comprising:
a housing;
an expandable reservoir located in the housing to contain therapeutic fluid, wherein the expandable reservoir defines a volume and is configurable between an empty state and a full state, wherein the expandable reservoir comprises a movable wall that moves in response to the expansion and contraction of the expandable reservoir between the empty state and the full state;
a sensor located in the housing to sense a signal representative of a distance between the sensor and the movable wall of the expandable reservoir; and
computing apparatus operably coupled to the sensor to determine the volume of the expandable reservoir based on the signal representative of a distance between the sensor and the movable wall of the expandable reservoir, wherein the housing further comprises a window portion defining at least a portion of the expandable reservoir, wherein the sensor transmits and receives the signal into and out of the expandable reservoir through the window portion.

16. The system of claim 15, wherein the computing apparatus is located in the housing.

17. The system of claim 15, further comprising an external device, wherein the computing apparatus is located in the external device and is operably coupled to the sensor wirelessly.

18. The system of claim 15, wherein sensor is a light-based sensor and the signal is a light signal.

19. The system of claim 15, wherein the reservoir comprises a fixed wall opposite the movable wall, wherein the fixed wall is in a fixed position with respect to the sensor.

* * * * *